(12) United States Patent
Forster et al.

(10) Patent No.: US 6,653,299 B1
(45) Date of Patent: Nov. 25, 2003

(54) LABELLED FACTOR XIIIA SUBSTRATES

(75) Inventors: Alan Michael Forster, High Wycombe (GB); Peter Knox, Chalfont St Giles (GB); Marivi Mendizabal, London (GB); Timothy Charles Richardson, Great Missenden (GB); Anthony Eamon Storey, Amersham (GB); Ian Andrew Wilson, Hitchin (GB); Susan Champion, Chesham (GB); Alex Gibson, Little Chalfont (GB); Benedicte Guilbert, Rickmansworth (GB)

(73) Assignee: Nycomed Amersham PLC, Buckinghamshire (GB)

( * ) Notice: Subject to any disclaimer, the term of this patent is extended or adjusted under 35 U.S.C. 154(b) by 0 days.

(21) Appl. No.: 09/341,915

(22) PCT Filed: Jan. 19, 1998

(86) PCT No.: PCT/GB98/00157

§ 371 (c)(1),
(2), (4) Date: Oct. 4, 1999

(87) PCT Pub. No.: WO98/31399

PCT Pub. Date: Jul. 23, 1998

(30) Foreign Application Priority Data

Jan. 21, 1997 (EP) .............................. 97300383

(51) Int. Cl.$^7$ .................. A61K 31/28; A61K 31/33; A61K 31/44; A61K 31/18; A61K 31/4965
(52) U.S. Cl. .................. 514/183; 514/255.01; 514/353; 514/492; 514/603; 514/626; 540/474; 544/390; 546/306; 556/37; 564/86
(58) Field of Search ................. 514/492, 603, 514/626, 183, 255.01, 353; 556/37; 564/86, 197; 540/474; 544/390; 546/306

(56) References Cited

U.S. PATENT DOCUMENTS 5,387,692 A   2/1995   Riley et al. .............. 548/313.7
5,993,774 A * 11/1999   Archer et al. .............. 424/1.65

FOREIGN PATENT DOCUMENTS

EP    0 229 718 A3    7/1987
EP    0 544 412 A2    6/1993
WO    WO 80/01685     8/1980

OTHER PUBLICATIONS

Pillai et al., "Some Observations on the Instability of $^{99m}$Tc–Complexes of Propylene Amine Oxime (PnAO)," *Nucl. Med. Biol.*, vol. 21, No. 7, pp. 997–1003 (1994).

Ramalingam et al., "Synthesis of Nitroimidazole Substituted 3,3,9,9–Tetramethyl–4,8–diazaundecane–2, 10–dione Dioximes (Propylene Amine Oximes, PnAOs): Ligands for Technetium–99m Complexes with Potential for Imaging Hypoxic Tissue," *Tetrahedron*, vol. 51, No. 10, pp. 2875–2894 (1995).

* cited by examiner

Primary Examiner—Peter O'Sullivan
(74) Attorney, Agent, or Firm—Marshall, Gerstein & Borun

(57) ABSTRACT

A complex of a radiometal or paramagnetic metal ion with a metal chelating agent such as a diaminedioxime has attached thereto a substituent of formula —(Y)$_m$—A—NHR, can function as a substrate for the fibrin-stabilizing Factor XIIIa. The complex is useful for the diagnosis or therapy of thrombosis, embolism, atherosclerosis, inflammation or cancer.

13 Claims, No Drawings

LABELLED FACTOR XIIIA SUBSTRATES

This application is a 371 of PCT/GB98/00157 filed Mar. 19, 1998.

The present invention relates to a class of compounds useful in the diagnosis of sites of thrombosis, embolism or infection, pharmaceutical formulations containing them, their use in the diagnosis of disease and methods for their preparation.

Prior approaches to thrombus imaging radiopharmaceuticals include radiolabelled fibrinogen or plasminogen; radiolabelled fragment E, of human fibrin; radiolabelled plasminogen activators such as tissue plasminogen activator (t-PA) and labelled anti-fibrin antibodies. Methods based on the detection of sites of platelet accumulation such as the administration of radiolabelled platelets (e.g. using $^{111}$In oxine) or radiolabelled anti-platelet antibodies have also been described. More recent efforts have focused on radiolabelled peptides or polypeptides such as the cell adhesion motif RGD (where R, G and D are the standard abbreviations for the amino acids arginine, glycine and aspartic acid respectively); platelet factor 4 or fragments thereof or anticoagulant peptides such as disintegrins.

Factor XIII is a plasma glycoprotein which is present in blood and certain tissues in a catalytically inactive (or zymogen) form. Factor XIII is transformed into its active form Factor XIIIa by thrombin in the presence of calcium ions. Factor XIIIa is also known as plasma transglutaminase, fibrinoligase or fibrin-stabilizing factor. The final step in the formation of a blood clot is the covalent crosslinking of the fibrin which is formed by the proteolytic cleavage of fibrinogen by thrombin. Fibrin molecules align and the enzyme Factor XIIIa catalyses covalent crosslinking of the $NH_2$ and $CO_2NH_2$ groups of lysyl and glutaminyl residues respectively giving structural rigidity to the blood clot. The crosslinking stabilises the fibrin clot structure and confers resistance to fibrinolysis. The crosslink formation is an important facet of normal blood coagulation and wound healing as well as pathological conditions such as thrombosis. It may also be implicated in atherosclerosis and tumour growth and metastasis. WO 91/16931 discloses that radiolabelled analogues of Factor XIII (in which the active site has been inactivated by amino acid substitution) are useful as thrombus imaging radiopharmaceuticals.

Factor XIIIa is also known to catalyse the incorporation of low molecular weight amines into the γ-glutamine sites of proteins. Thus such low molecular weight amines function as competitive inhibitors of the Factor XIIIa-induced glutaminyl crosslinking of proteins. A range of synthetic amines have been described which are competitive inhibitors of the uptake of labelled putrescine (1,4-butanediamine) into N,N'-dimethylcasein catalysed by pig liver transglutaminase [L. Lorand et al., Biochem., 18, 1756(1979)].

The possible use of radiolabelled diamines of formula $H_2N(CH_2)_nNHR^*$ (n and R* undefined) as potential clot imaging agents was disclosed by Rhodes et al (Chapter 54, p.521 in "Radiopharmaceuticals", G. Subramanian, B. A. Rhodes, J. F. Cooper & V. J. Sodd [Eds], Society of Nuclear Medicine Inc., 1975). They envisaged that a radiolabelled amine which was an inhibitor of the crosslinking of fibrin could form a substrate for Factor XIIIa and hence become attached to the fibrin of blood clots. U.S. Pat. No. 4,406,075 (Mallinckrodt) discloses radiolabelled aliphatic amines for blood clot imaging of formula:

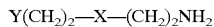
Y(CH$_2$)$_2$—X—(CH$_2$)$_2$NH$_2$ where X is O, S, Se*, Te* or lower alkylene.

When X is Se* or Te*, Y is a hydrocarbylamino group, and when X is O, S or lower alkylene, Y is a radioiodinated hydrocarbylamino group (or salt thereof).

(* denotes a radioactive atom).

WO 89/00051 (Cytrx Biopool Ltd.) claims a method for targeting fibrin deposits using a labelled compound which is covalently bound to fibrin by Factor XIIIa. The fibrin binding compound is stated to be "any peptide that is a substrate for the blood enzyme commonly known as Factor XIIIa".

It has now been discovered that metal complexes with suitable pendant functional groups can also function as substrates for the enzyme Factor XIIIa. Since Factor XIIIa is only released at pathological sites from an inactive precursor, targeting this enzyme provides a means of targeting a diagnostic imaging agent to the site of Factor XIIIa release.

The present invention provides in one aspect a metal complexing agent having attached thereto at least one substituent of formula

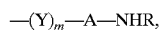
—(Y)$_m$—A—NHR, where:

Y is the same or different at different locations within the molecule and is independently chosen from: an A group, a $C_{4-8}$ cycloheteroalkylene group, a $C_{4-8}$ cycloalkylene group, a $C_{5-12}$ arylene group, a $C_{3-12}$ heteroarylene group, or a polyalkyleneglycol, polyactic acid or polyglycolic acid moiety, m is an integer of value 0–20, A is a 3–10 atom chain of units selected from —CR$_2$—, —CR=CR—, —C≡C—, —NRCO—, —CONR—, —SO$_2$NR—, —NRSO$_2$—, or —CR$_2$ZCR$_2$— where Z is —CH$_2$—, O, S, Se or —NR—, R is the same or different at different locations within the molecule and is independently chosen from H, $C_{1-4}$ alkyl, $C_{1-4}$ alkenyl, $C_{1-4}$ alkynyl, $C_{1-4}$alkoxyalkyl or $C_{1-4}$ hydroxyalkyl, with the proviso that the complexing agent does not also have attached thereto a hypoxia localising moiety.

The invention also provides a metal complex of one or more radiometal or paramagnetic metal ions with the metal complexing agent as defined; both as a new compound per se and also for use in the diagnosis or therapy of thrombosis, embolism, atherosclerosis, inflammation or cancer.

Preferably the metal complexing agent is a metal chelating agent, for example a diaminedioxime. In preferred substituents, A is

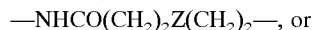
—NHCO(CH$_2$)$_2$Z(CH$_2$)$_2$—, or

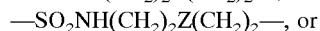
—SO$_2$NH(CH$_2$)$_2$Z(CH$_2$)$_2$—, or

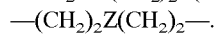
—(CH$_2$)$_2$Z(CH$_2$)$_2$—.

Preferably Z is CH$_2$. Particularly preferred substituents have the formula

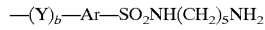
—(Y)$_b$—Ar—SO$_2$NH(CH$_2$)$_5$NH$_2$ where b is an integer of value 0 to 19 and Ar is an arylene or heteroarylene group.

The complexing agents of the present invention preferably only have a single type of targeting molecule attached, i.e. the —(Y)$_m$—A—NHR substituent. Other substituents on the complexing agent may be present, but the —(Y)$_m$—A—NHR substituent is the one which is expected to be primarily responsible for the biolocalisation properties. The —(Y)$_m$—A—NHR substituent may be attached to either the backbone which connects metal donor atoms of a metal complexing or chelating agent, or to a metal donor atom of the metal complexing or chelating agent.

When Y includes a biocompatible, hydrophilic polymer such as a polyalkyleneglycol, polylactic acid or polyglycolic acid, this polymeric linking group may be useful to prolong the residence time of the metal complex in the bloodstream, ie. to slow down the rate of clearance from the blood following administration. The hydrophilic polymer is preferably a polyalkyleneglycol, most preferably polyethyleneglycol (PEG). The hydrophilic polymer preferably has a molecular weight of 2,000 to 20,000 Daltons.

The metal complex of the present invention may contain one or more metal ions which may be the same or different. Thus in some circumstances polynuclear complexes may have advantageous properties such as certain metal clusters which have superparamagnetic properties and are hence particularly useful as MRI contrast agents. Preferred metal complexes of the present invention involve only a single metal ion. When the metal of the metal complex is a radiometal, it can be either a positron emitter (such as $^{68}$Ga or $^{64}$Cu) or a γ-emitter such as $^{99m}$Tc, $^{111}$In, $^{113m}$In or $^{67}$Ga. Suitable metal ions for use in MRI are paramagnetic metal ions such as gadolinium(III) or manganese(II). Most preferred radiometals for diagnostic imaging are γ-emitters, especially $^{99m}$Tc. Metal complexes of certain radionuclides may be useful as radiopharmaceuticals for the radiotherapy of various diseases such as cancer or the treatment of thrombosis or restenosis. Useful radioisotopes for such radiotherapeutic applications include: $^{90}$Y, $^{89}$Sr, $^{67}$Cu, $^{186}$Re, $^{188}$Re, $^{169}$Er, $^{153}$Sm and $^{198}$Au. Whichever metal complex is chosen, it is strongly preferred that it is bound to the Factor XIIIa substrate in such a way that it does not undergo facile metabolism in blood with the result that the metal complex is cleaved from the Factor XIIIa substrate before the labelled Factor XIIIa substrate reaches the desired in vivo site to be imaged. The Factor XIIIa substrate is therefore preferably covalently bound to the metal complexes of the present invention.

The metal ions of the present invention are complexed using a metal complexing agent or more preferably a metal chelating agent. The chelating agents comprise 2–10 metal donor atoms covalently linked together by a non-coordinating backbone. Preferred chelating agents have 4–8 metal donor atoms and have the metal donor atoms in either an open chain or macrocyclic arrangement or combinations thereof. Most preferred chelating agents have 4–6 metal donor atoms and form 5- or 6-membered chelate rings when coordinated to the metal centre. Such polydentate and/or macrocyclic chelating agents form stable metal complexes which can survive challenge by endogenous competing ligands for the metal in vivo such as transferrin or plasma proteins. Alternatively it is possible to use monodentate complexing agents that form strong stable complexes with the desired metal ions. Examples of known complexing agents of this kind, which are particularly suitable for use with $^{99m}$Tc, are hydrazines, phosphines, arsines and isonitriles. Unlike chelating agents, complexing agents do not necessarily occupy all the co-ordination centres of the metal ion.

The metal complex should also preferably be of low lipophilicity (since high lipophilicity is often related to non-specific uptake), and exhibit low plasma protein binding (PPB) since plasma-bound label again contributes to undesirable high, non-specific blood background for the imaging agent.

Examples of suitable chelating agents are diaminedioximes (U.S. Pat. No. 4,615,876) or such ligands incorporating amide donors (WO 94/08949); the tetradentate ligands of WO 94/22816; $N_2S_2$ diaminedithiols, diamidedithiols or amideaminedithiols; $N_3S$ thioltriamides; $N_4$ ligands such as tetraamines, macrocyclic amine or amide ligands such as cyclam, oxocyclam (which forms a neutral technetium complex) or dioxocyclam; or dithiosemicarbazones. The above described ligands are particularly suitable for technetium, but are useful for other metals also. Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. The ligand may also comprise a short sequence of amino acids such as the Cys/amino acid/Cys tripeptide of WO 92/13572 or the peptide ligands described in EP 0719790 A2

It is well known to prepare chelating agents which have attached thereto a functional group ("bifunctional chelates"). Functional groups which have been attached to chelating agents include: amine, carboxylic acid, cyanate, thiocyanate, maleimide and active ester such as N-hydroxysuccinimide. Examples of chelate-amine conjugates for diaminedioxime ligands are given in WO 95/19187. The ligands of the present invention can be prepared by reaction of a bifunctional compound which contains both an amine group (preferably protected by use of suitable protecting groups known to those skilled in the art), and a reactive group such as a sulphonyl chloride, acid chloride, active ester or an alkyl/benzyl halide. The reactive group can then be coupled to either the pendant amine group of a bifunctional chelate, or used to derivatise one or more of the amine donor atoms of a N-containing ligand. Alternatively, a mono-protected diamine could be reacted with a bifunctional chelate with a pendant active ester or carboxyl group to give the protected amine group linked to the ligand system via an amide bond. In both synthetic routes outlined above, the resulting ligand-protected amine conjugate is then deprotected under suitable conditions to give the desired amine-functionalised ligand.

The metal complexes of the present invention may be prepared by reacting a solution of the metal in the appropriate oxidation state with the ligand at the appropriate pH. The solution may preferably contain a ligand which complexes weakly to the metal (such as chloride, gluconate or citrate) i.e. the metal complex is prepared by ligand exchange or transchelation. Such conditions are useful to suppress undesirable side reactions such as hydrolysis of the metal ion. When the metal ion is $^{99m}$Tc, the usual starting material is sodium pertechnetate from a $^{99}$Mo generator. Technetium is present in $^{99m}$Tc-pertechnetate in the Tc(VII) oxidation state, which is relatively unreactive. The preparation of technetium complexes of lower oxidation state Tc(I) to Tc(V) therefore usually requires the addition of a suitable reducing agent such as stannous ion to facilitate complexation. Further suitable reductants are described below.

Thus the present invention relates to diagnostic agents for imaging sites in the mammalian body where the enzyme Factor XIIIa is up-regulated and fibrin is deposited. The present agents are particularly useful for the diagnostic imaging of the human body. The agents comprise substrates for the enzyme Factor XIIIa which are labelled with a metal complex suitable for external imaging such as a radiometal (for scintigraphy) or a paramagnetic metal ion (for MRI). The metal complex of the present invention has a pendant amino functional group which is available for covalent linking to protein glutamyl carboxamide groups by the enzyme Factor XIIIa. The intimate relationship of fibrin and Factor XIIIa highlights the potential use of the agents of the present invention for the diagnosis of disease states where there is both fibrin deposition or accumulation and up-regulation of Factor XIIIa. Increased fibrin deposition is known to be characteristic of diseases such as thrombosis, atherosclerosis, fibrotic liver, and disseminated intravascular coagulation. Fibrin is also deposited at sites of tissue inflammation associated with many disease processes, such as infection, autoimmune disease or cancer. Factor XIIIa and tissue transglutaminase are up regulated during known physiological conditions. During apoptosis and generation of new matrix protein structures elevated levels of the enzymes are seen. The present agents may thus also be used for the detection of apoptosis and diseases states such as arthritis where increased matrix protein deposition occurs. Since Factor XIIIa is up-regulated at the site of interest in vivo (i.e. thrombus, embolism etc.) this provides a localisation mechanism for the metal complexes of the present invention. The covalently linked metal complexes can then be imaged externally by radionuclide scintigraphy or magnetic resonance imaging (MRI) hence providing a non-invasive means of diagnosing the disease site.

The present invention also relates to kits for the preparation of metal complexes linked to Factor XIIIa substrates. The kits are designed to give sterile products suitable for human administration, e.g. via injection into the bloodstream. Possible embodiments are discussed below. When the detectable moiety is $^{99m}$Tc, the kit would comprise a vial containing the free ligand or chelating agent for the metal together with a pharmaceutically acceptable reducing agent such as sodium dithionite, sodium bisulphite, ascorbic acid, formamidine sulphinic acid, stannous ion, Fe(II) or Cu(I), preferably a stannous salt such as stannous chloride or stannous tartrate. Alternatively, the kit could contain a metal complex which, upon addition of the radiometal or paramagnetic metal, undergoes transmetallation (i.e. ligand exchange) giving the desired product. For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation.

The agents of the present invention may also be provided in a unit dose form ready for human injection and could for example be supplied in a pre-filled sterile syringe. When the detectable moiety is a radioactive isotope such as $^{99m}$Tc, the syringe containing the unit dose would also be supplied within a syringe shield (to protect the operator from potential radioactive dose).

The above kits or pre-filled syringes may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid) or bulking agents for lyophilisation (such as sodium chloride or mannitol).

The following Examples illustrate the preparation of compounds of the present invention and their use in imaging. The syntheses of particular compounds of the present invention are given in Examples 1–20, and their radiolabelling with $^{99m}$Tc in Examples 21–23. Evidence for uptake in blood clots in vitro and in vivo is given in Examples 25, 26, 28 with normal rat biodistribution of the radiolabelled compounds reported in Example 27. The in vivo results of Example 27 indicate a rapid clearance of the compounds from the blood. The kinetics of disappearance of radioactivity from key background organs (e.g. lung, heart, muscle) followed a pattern similar to that of the blood. The analyses of a variety of organs did not show any specific accumulation, with the exception of those compounds that excreted primarily by the hepatobiliary system (HBS) which tended to accumulate in the liver. The rapid background clearance and lack of organ accumulation of the compounds of the present invention are important characteristics for diagnostic imaging agents since the area of interest (e.g. thrombus) is therefore more clearly delineated. The percentage of the injected dose (%ID) found in the blood at 60 minutes post injection for the compounds varies between 0.3–2.5% with most of the injected dose excreted within 4 h post-injection. The majority of compounds have the HBS as the main route of excretion with 70–90%ID excreted by this route within 4 h but in several compounds (Compound 17, Compound 24, Compound 25) the urinary system is the major excretory route with 50–90%ID being excreted within 4 h. The biological half-life of these compounds does vary, but for all of them it is very short. The relatively short half-life of these compounds and lack of accumulation at key organs is important for the possible use in diagnostic imaging of thrombi.

The compounds of the present invention exhibit clot uptake in an animal model (Example 28). Higher clot uptake (%ID/g 0.2–0.3%) is seen for those tracers which have a slower clearance rate. The clot/background ratios are, in general, favourable for imaging (i.e. >1) but for those compounds excreted via the HBS the clot/liver ratios are poorer.

| Ligand | R | Compound |
|---|---|---|
| [structure] | H | 2 |

-continued

| Ligand | R | Compound |
|---|---|---|
| | (4-aminobutyl)sulfamoyl-benzoyl group | 3 |
| | 6-aminohexanoyl group | 4 |
| | N-(6-aminohexanoyl)-phenylalanyl group | 5 |
| | 4-(6-aminohexanamido)benzoyl group | 6 |
| | 4-((4-((5-aminopentyl)sulfamoyl)benzamido)methyl)cyclohexanecarbonyl group | 8 |
| | 4-(N-(2-(2-aminoethylthio)ethyl)sulfamoyl)benzoyl group | 9 |
| | Ser-Ser-Ser-(4-((5-aminopentyl)sulfamoyl)benzoyl) group | 10 |

-continued
| Ligand | R | Compound |
|---|---|---|
| | 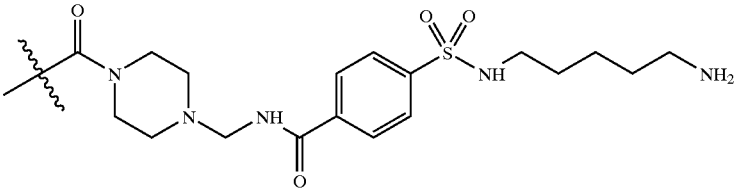 | 11 |
| | 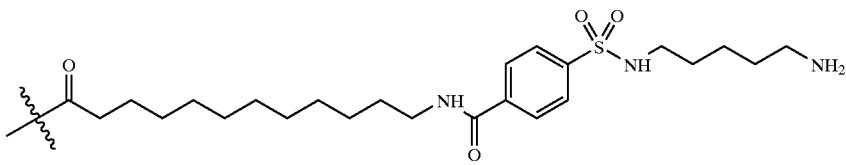 | 13 |
| | 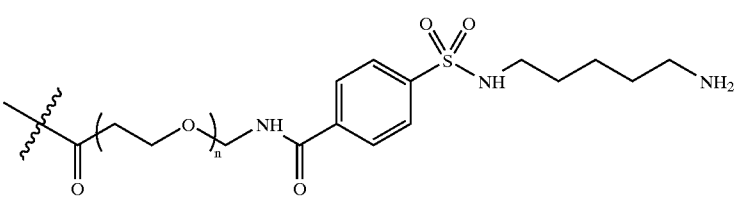 | 14 |
| 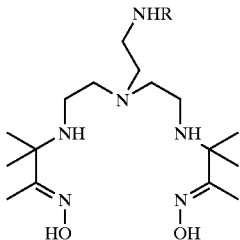 | 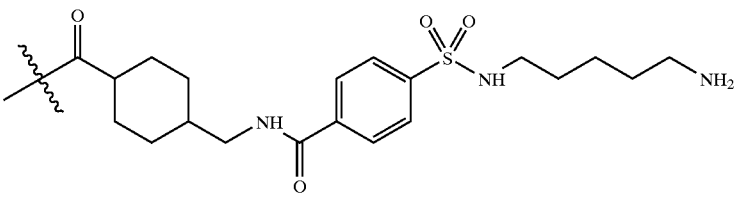 | 16 |
| | 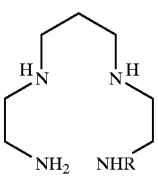 | 17 |
| 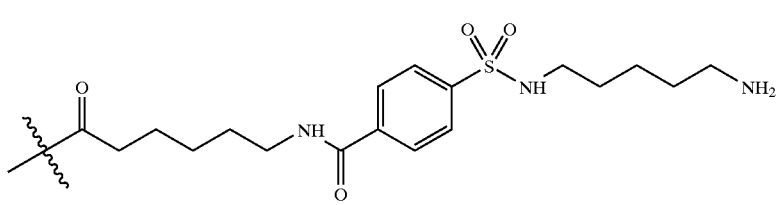 | | 18 |
| | | 19 |

-continued

| Ligand | R | Compound |
|---|---|---|
| 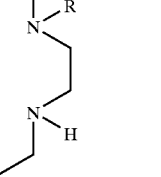 | 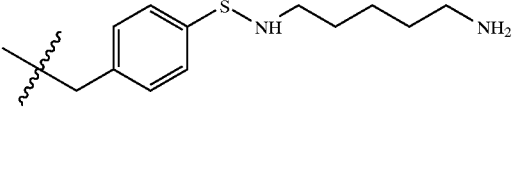 | 20 |
| 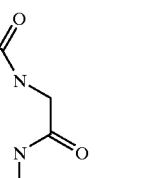 | 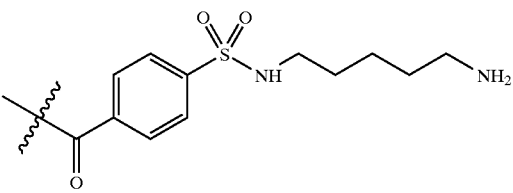 | 23 |
| 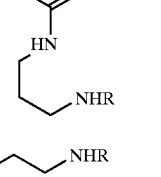 | 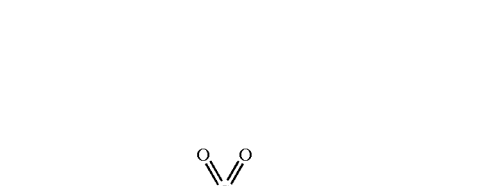 | 24 |
|  | 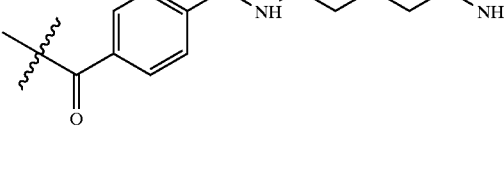 | 25 |

EXPERIMENTAL

Example 1

Synthesis of 3,3,6,9,9-pentamethyl-6-(4-(N-(5-aminopentyl)amidosulphonyl)benzamidomethyl)-4,8-diazaundecane-2,10-dione dioxime, trifluoroacetate salt (Compound 3).

(a): Synthesis of 4-(N-(5-N'-$^t$butoxycarbonyl aminopentyl) amidosulphonyl)benzoic acid (Compound 1)

To a solution of mono-N-$^t$butoxycarbonyl-1,5-diaminopentane (543 mg, 2.69 mmol; Fluka Chemicals) in dichloromethane (10 ml) was added triethylamine (748 ml, 5.37 mmol, 2 eq). A slurry of 4-chlorosulphonylbenzoic acid (592 mg, 2.69 mmol, 1 eq) in dichloromethane (3 ml) was added and the flask rinsed with more dichloromethane (5 ml). The resulting yellow solution was stirred at room temperature for 19 hours. The solvent was removed in vacuo and the residue was taken up in 10%aq HCl. It was then extracted with three portions of EtOAc. The combined organic layers were dried (Na$_2$SO$_4$), filtered and evaporated. The residue was then recrystallised from ethyl acetate/petrol to afford the title compound as a buff powder (667 mg, 64%).

δH (270 MHz, CD$_3$OD) 1.16–1.5 (15H, m, —C(C$\underline{H}_3$)$_3$, —(C$\underline{H}_2$)$_3$—), 2.86 (2H, t, J 8.44 Hz, —C$\underline{H}_2$NHBoc), 2.94 (2H, t, J 8.44 Hz, —SO$_2$NHC$\underline{H}_2$—), 7.92 (2H, d, J 8.44 Hz, aromatic protons), 8.19 (2H, d, J 8.44 Hz, aromatic protons).

(b): Synthesis of Compound 3

To a solution of Compound 1 (202 mg, 0.52 mmol, 1.1 eq) and Py-BOP (272 mg, 0.52 mmol, 1.1 eq) in DMF (5 ml) under N$_2$ was added DIPEA (91 ml, 0.52 mmol, 1.1 eq).The mixture was stirred for 2 hours at room temperature, when HPLC showed the formation of a new species with retention time 14.7 mins (System A). A solution of Compound 2 (6-aminomethyl-3,3,6,9,9-pentamethyl-4,8-diazaundecane-2,10-dione dioxime, 150 mg, 0.48 mmol; prepared as described in WO 95/19187) in DMF (2 ml) was added and the mixture was stirred for 3 hours at room temperature. After this time HPLC showed the disappearance of the peak at 14.7 mins, and a further new species at 10.1 mins. The reaction mixture was poured into a saturated solution of sodium bicarbonate and extracted with three portions of ethyl acetate. The combined organic layers were dried (Na$_2$SO$_4$), filtered and evaporated. The crude material was taken up in ethyl acetate (20 ml) from which a 10 ml aliquot of was taken and evaporated to dryness. It was then treated with TFA (3 ml) for 3.5 hours. After this time had elapsed, HPLC (System A) showed that all the starting material had been consumed. The mixture was evaporated to dryness and purified by RP-HPLC (System B).

Mass Spec. Analysis (FAB+)
Theoretical molecular weight: 583.6
Experimental molecular weight [M+H]+584.3

Example 2

Synthesis of 3,3,6,9,9-pentamethyl-6-N-(6-aminohexoyl)aminomethyl-4,8-diazaundecane-2,10-dione dioxime (Compound 4)

Synthesis is as described for Compound 3 but, to a solution of Compound 2 in DMF (2 ml) were successively added BOC-6-aminohexanoic acid, Py-BOP and DIPEA. The title compound was obtained by TFA deprotection and RP-HPLC as described for Compound 3.

Mass Spec. Analysis (FAB+)
Theoretical molecular weight: 428.6
Experimental molecular weight [M+H]+429.4

Example 4

Synthesis of 3,3,6,9,9-pentamethyl-6-N-[N-(6-aminohexanoyl)-D-phenylalanyl]aminomethyl4,8-diazaundecane-2,10-dione dioxime (Compound 5)

BOC-6-aminohexanoic acid (2.14 g, 9.25 mmol) was coupled to D-phenylalanine benzyl ester hydrochloride (2.7 g, 9.25 mmol) with Py-BOP in the presence of DIPEA, and the resulting product was hydrogenated in 95% ethanol at atmospheric pressure in the presence of 10% palladium over charcoal to afford BOC-6-aminohexanoyl-D-phenylalanine (3.35 g, 85%). The title compound was obtained by coupling BOC-6-aminohexanoyl-D-phenylalanine to Compound 2, deprotection and RP-HPLC as described for Compound 3.

Mass Spec. Analysis (FAB+)
Theoretical molecular weight: 575.8
Experimental molecular weight [M+H]+575.9

Example 5

Synthesis of 3,3,6,9,9-pentamethyl-6-N-[4-N-(6-aminohexanoyl)aminobenzoyl]aminomethyl-4,8-diazaundecane-2,10-dione dioxime (Compound 6)

BOC-6-aminohexanoic acid was coupled to 4-aminobenzoic acid benzyl ester hydrochloride through a symmetrical anhydride in the presence of DIPEA and a catalytic amount of DMAP, and the resulting product was hydrogenated in 95% ethanol at atmospheric pressure in the presence of 10% palladium over charcoal to afford BOC-6-aminohexanoyl-4-aminobenzoic acid. The title compound was obtained by coupling BOC-6-aminohexanoyl-4-aminobenzoic acid to Compound 2, TFA deprotection and RP-HPLC purification as described for Compound 3.

Mass Spec. Analysis (FAB+)
Theoretical molecular weight: 547.7
Experimental molecular weight [M+H]+547.8

Example 6

Synthesis of 3,3,6,9,9-pentamethyl-6-N[4-N-{(4-N-(5-aminopentyl)amidosulphonyl)benzoyl}aminomethylcyclohexylcarbonyl]aminomethyl-4,8-diazaundecane-2,10-dione dioxime (Compound 8)

(a): Synthesis of 4-(N-(5-N'-$^t$butoxycarbonylaminopentyl)amidosulphonyl)benzamidomethyl-6-cyclohexane carboxylic acid (Compound 7)

To a solution of trans4-(aminomethyl)cyclohexane carboxylic acid (1 g, 6.36 mmol) in 4M NaOH (15 ml) at 0° C. was added BOC anhydride (1.46 ml, 6.36 mmol, 1 eq). The mixture was stirred at 0° C. and allowed to warm to room temperature over the course of 24 hours. A white precipitate was formed as the reaction progressed, which redissolved with time. After 24 hours, the mixture was acidified to pH3 with 10% HCl. At pH6 a lot of white solid was observed. This solid was extracted into EtOAc, and acidification of the aqueous phase then continued. When the mixture reached pH3, it was extracted with three portions of EtOAc. The combined organic extracts were dried ($Na_2SO_4$), filtered and evaporated to afford the desired product (1.384 g, 85%), which was used without further purification.

To a solution of trans-4-(N-BOC-aminomethyl) cyclohexane carboxylic acid (1.359 g, 5.28 mmol) in dichloromethane (15 ml), was added DMAP (catalytic amount) and benzyl alcohol (550 ml, 5.28 mmol, 1 eq). DCC (1M soln. in CH2Cl2, 5.28 ml, 5.28 mml, 1 eq) was added and the mixture was stirred at room temperature for 3 hours. The reaction mixture was then filtered and the filtrate evaporated. The residue was purified by flash column chromatography (eluent 3:1 petrol:EtOAc) to afford the desired product as a yellow oil which solidified to give an off-white solid on standing (1.742 g, 95%).

To a solution of trans-4-(N-BOC-aminomethyl) cyclohexane carboxylic acid, benzyl ester (1.401 g, 4.03 mmol) in dichloromethane (5 ml) was added TFA (10 ml). The solution was stirred at room temperature for 10 minutes. The solution was evaporated to dryness affording the product as a yellow oil (1.44 g, 99%).

To a solution of trans-4-(aminomethyl)cyclohexane carboxylic acid, benzyl ester (0.5 g, 1.38 mmol) in dry DMF (2 ml) under $N_2$ was added Compound 1 (533 mg, 1.38 mmol, 1 eq), HBTU (523 mg, 1.38 mmol, 1 eq) and DIPEA (1.7 ml, 9.76 mmol, 7 eq). The reaction mixture was stirred at room temperature for 15 hours. The mixture was diluted with dichloromethane (20 ml) and extracted with three portions of 10% citric acid solution. The organic phase was then washed twice with sat. $NaHCO_3$ and then with brine. The organic layer was dried ($Na_2SO_4$), filtered and evaporated. The residue was purified by flash column chromatography (eluent 7:3 EtOAc:petrol) to afford the desired product as an off-white foam (0.554 g, 65%). To a solution of this foam (437 mg, $7.09 \times 10^{-4}$ mol) in ethanol (15 ml) was added 10% palladium over charcoal (440 mg) and cyclohexene (720 ml, 7.09 mmol, 10 eq). The mixture was heated to reflux temperature for 4.5 hours, filtered and then evaporated to dryness to afford Compound 7 as a white solid (375 mg, 100%). This solid was used without further purification.

$\delta$H ($CDCl_3$, 300 MHz): 7.88 (4H, s, aromatic), 6.667 (1H, br.s, cyclohexyl-$CH_2N\underline{H}$), 4.87 (1H, t, J 9.0 Hz, $SO_2NH$), 4.54(1H, br.s, NHBoc), 3.28 (2H, t, J 9.0 Hz, $SO_2NHC\underline{H}_2$), 2.93–3.03 (4H, m, $C\underline{H}_2NH$, $C\underline{H}_2NHBoc$), 2.21–2.33 (1H, m, $C\underline{H}CO_2H$), 1.85–2.06 (4H, m, 2×ring$CH_2$), 0.96–1.66 (20H, m, 2×ring $CH_2$, ring CH, BOC —$(CH_2)_3$—).

(b): Synthesis of Compound 8

Compound 7 (150 mg, $2.85 \times 10^{-4}$ mol), Compound 2 (90 mg, $2.85 \times 10^{-4}$ mol, 1 eq) and HBTU (108 mg, $2.85 \times 10^{-4}$ mol, 1 eq) were dissolved in DMF (2 ml) under $N_2$. DIPEA (250 ml, 1.43 mmol, 5 eq) was added and the reaction mixture was stirred at room temperature for 5 hours and followed by RP-HPLC (System D). The crude reaction mixture was purified by RP-HPLC (System E) to afford the desired protected product (142 mg, 63%). The title compound was obtained by TFA deprotection as described for Compound 2. The crude product was purified by RP-HPLC (System F) to afford the desired product as a white solid (8 mg, 23%).

Mass Spec. Analysis (FAB+)
Theoretical molecular weight: 722.0
Experimental molecular weight [M+H]+723.0

Example 7

Synthesis of 3,3,6,9,9-pentamethyl-6-(4-(N-[(S-aminoethyl)thioethyl]amidosulphonyl) benzamidomethyl)-4,8-diazaundecane-2,10-dione dioxime (Compound 9)

To a solution of thiacadaverine (0.5 g, 4.16 mmol) in dichloromethane (5 ml) at −78° C. under $N_2$ was added slowly a solution of BOC anhydride (478 ml, 2.08 mmol, 0.5 eq) in dichloromethane (1 ml). The reaction mixture was stirred at −78° C. for 5 hours, then allowed to warm gradually to room temperature for 18 hours. During this time, the reaction mixture turned opaque. The solvent was removed by evaporation, and the white residue was purified by flash column chromatography (eluent 80:20:1 $CH_2Cl_2$:MeOH:$NH_3$) to afford the product as a yellow oil (388 mg, 85%). To mono-N-Boc-thiacadaverine (369 mg, 1.68 mmol) in dichloromethane (5 ml) was added triethylamine (470 ml, 3.36 mmol, 2 eq) and a slurry of 4-chlorosulphonylbenzoic acid in dichloromethane (2 ml) and reacted as described for Compound 1(429 mg, 63%). The title compound was obtained as described for Compound 8 by coupling the above acid (150 mg, $3.71 \times 10^{-4}$ mol), Compound 2 (117 mg, $3.71 \times 10^{-4}$ mol, 1 eq) and HBTU (141 mg, $3.71 \times 10^{-4}$ mol, 1 eq) in DMF (2 ml), with DIPEA (330 ml, 1.85 mmol, 5 eq). TFA deprotection and RP-HPLC (System F) purification were as described for Compound 3 (27 mg, 52%).

Mass Spec. Analysis (FAB+)
Theoretical molecular weight: 601.0
Experimental molecular weight [M+H]+602.0

Example 8

Synthesis of 3,3,6,9,9-pentamethyl-6-N-[N-(4-N-(5-aminopentyl)amidosulphonyl)benzoyl-D-serine-D-serine-D-serine]aminomethyl4,8-diazaundecane-2,10-dione dioxime (Compound 10)

4-(BOC-5-aminopentyl)amidosulphonylbenzoyl-D-Ser(tBu)l-D-Ser(tBu)l-D-Ser(tBu)-OH was assembled on a 2-chlorotrityl resin by anchoring Fmoc-D-Ser(tBu) to the resin, and by successive deprotections/couplings cycles (as described in P. Lloyd-Williams, F. Albericio and E. Girald; *Chemical Approaches to the Synthesis of Peptides and Proteins*, CRC Press, 1997) with Fmoc-D-Ser(tBu), Fmoc-D-ser(tBu), Fmoc-D-ser(tBu) and Compound 1. The protected compound was obtained by 1% TFA in dichloromethane cleavage. The title compound was obtained by coupling with Py-BOP of the protected intermediate to Compound 2, TFA deprotection and RP-HPLC purification as described for Compound 3.

Mass Spec. Analysis (FAB+)
Theoretical molecular weight: 845.0
Experimental molecular weight [M+H]+844.7

Example 9

Synthesis of 3,3,6,9,9-pentamethyl-6-N-[4-N{4-(N-(5-aminopentyl)amidosulphonyl) benzoyl}aminomethylpiperazinylcarbonyl] aminomethyl-4,8-diazaundecane-2,10-dione dioxime (Compound 11)

The pseudo-protected peptide was obtained as in Example 8. The title compound was obtained by coupling to Compound 2, TFA deprotection and RP-HPLC purification as described for compound 3.

Mass Spec. Analysis (FAB+)
Theoretical molecular weight: 709.9
Experimental molecular weight [M+H]+709.9

Example 10

Synthesis of 3,3,6,9,9-pentamethyl-6-N{4-(N-(5-aminopentyl)amidosulphonyl) benzoyl}amidododecanoyl]aminomethyl-4,8-diazaundecane-2,10-dione dioxime (Compound 13)

(a): Synthesis of 4-(N-(5-N'-$^t$butoxycarbonylaminopentyl) amidosulphonyl) benzoyl amidododecanoic acid (Compound 12)

12-aminododecanoic acid (1 g, 4.64 mmol) was BOC protected as described in Example 7. (0.467 g, 35%). The benzyl ester of the above was formed as described in Example 6 to afford the desired compound as a viscous oil (0.821 g). To a solution of the N-BOC-12-aminododecanoic acid, benzyl ester (821 mg) in dichloromethane (5 ml) was added TFA (5 ml) dropwise with stirring. The solvents were then removed in vacuo to afford the desired product. This product was used without any further purification. To a solution of the resulting crude product (1 g) in DMF (3 ml) under $N_2$ was added Compound 1 (1.27 g, 3.29 mmol), HBTU (1.24 g, 3.27 mmol) and DIPEA (2 ml, 11.48 mmol). The reaction was stirred at room temperature until TLC (3:7, petrol:EtOAc) indicated that the reaction was complete. The reaction mixture was diluted with dichloromethane, then washed with three portions of 10% citric acid solution. The organic phase was washed with saturated sodium bicarbonate solution and finally with brine. The organic layer was dried ($Na_2SO_4$), filtered and evaporated. The crude residue was subjected to flash column chromatography (3:7, petrol:EtOAc) to afford the desired compound as a yellow solid (1.433 g, 66%).

To a solution of the benzyl protected compound (1.4 g, 2.07 mmol) in ethanol (20 ml) was added 10% palladium over charcoal (1.4 g) and cyclohexene (1 ml, 9.87 mmol). The reaction mixture was heated at reflux temperature until TLC (3:7, petrol:EtOAc) indicated that the reaction was complete. The reaction mixture was then cooled and filtered. The filtrate was concentrated in vacuo to afford an oily yellow residue which was purified by RP-HPLC (System G) to afford the desired product (80 mg).

Mass Spec. Analysis (ES−)
Theoretical molecular weight: 583.0
Experimental molecular weight [M−H]+582.0

(b): Synthesis of Compound 13

To a solution of Compound 12 (70 mg, $1.2 \times 10^{-4}$ mol), Compound 2 (50 mg, $1.58 \times 10^{-4}$ mol, 1.3 eq) and HBTU (59 mg, $1.56 \times 10^{-4}$ mol, 1.3 eq) in dry DMF (4 ml) under $N_2$ was added DIPEA (135 mi, $9.13 \times 10^{-4}$ mol, 6.5 eq). The reaction mixture was stirred at room temperature and then purified by RP-HPLC (System G) to afford the intermediate as a white solid (60 mg, 57%). The title compound was obtained by TFA deprotection as described for Compound 3 and purified by RP-HPLC (System H) (10 mg, 23%).

Mass Spec. Analysis (ES+)
Theoretical molecular weight: 780.0
Experimental molecular weight [M+H]+781.6

Example 11

Synthesis of 3,3,6,9,9-pentamethyl-6-N-[α-N-(4-N-(5-aminopentyl)amidosulphonyl)benzoyl)amino-polyethyleneglycol)-ω-carbonyl]aminomethyl-4,8-diazaundecane-2,10-dione dioxime (Compound 14)

A solution of α-N-(tert-butoxycarbonyl)-poly(ethylene glycol)amino-ω-succinimidyl carbonate (500 mg, ~147 mmol) and Compound 2 (46.3 mg, 147 mmol) in dry THF (5 ml) was refluxed for 5 hours under $N_2$. The reaction mixture was reduced in vacuo leading to a white solid which was purified by flash chromatography ($^1$PrOH/NH$_3$/H$_2$O, 10:1:1) to give a white solid (456 mg, 86%). 37% HCl (1.34 ml) was added dropwise to an ice cold solution of the above (520 mg, ~144 mmol) in methanol (3.16 ml). The solution was then stirred at room temperature for 4 hours. The reaction mixture was basified to pH 10 by addition of 4M NaOH (4.18 ml), and the resulting product was isolated by RP-HPLC (System I). To a solution of the above (100 mg, 28.6 mmol) and compound 1 (11 mg, 28.6 mmol) in DMF (2 ml) was added HBTU (10.8 mg, 28.6 mmol) and DIPEA (25 ml, 143 mmol). The reaction mixture was stirred at room temperature, under $N_2$, for 22 hours then diluted with dichloromethane (20 ml), washed with NaHCO$_3$ (10 ml), water (10 ml), and brine (10 ml). The organic layer was reduced in vacuo and the residue was purified by RP-HPLC (System J) to give a colourless oil (36.8 mg, 33%). The oil (36.8 mg, ~9.5 mmol) was dissolved in a solution of 3M HCl in methanol (600 ml) and stirred at room temperature for 5.5 hours before the reaction mixture was basified to pH ~10 by addition of 4M NaOH (550 ml). The title compound was obtained by RP-HPLC (System K) as a white gum (29.5 mg, 82%).

Mass Spec. Analysis (MALDI-TOF)

Theoretical molecular weight range: 3000–5000

Experimental molecular weight range [M+H]+3000–5000

Example 12

Synthesis of 3,3,11,11-tetramethyl-7-(4-N-(5-aminopentyl)-amidosulphonyl)benzamidoethyl-4,7,10-triazatridecane-2,12-dione dioxime (Compound 16)

(a): Synthesis of 3,3,11,11-tetramethyl-7-aminoethyl-4,7,10-triazatridecane-2,12-dionedioxime (Compound 15)

To a solution of tris-(2-aminoethyl)amine (1 ml, 6.68 mmol) in acetonitrile (10 ml) was added sodium bicarbonate (1.12 g, 13.36 mmol, 2 eq). A solution of 3-chloro-3-methyl-2-nitrosobutane (1.359 g, 10.02 mmol, 1.5 eq) in dry acetonitrile (5 ml) was added slowly. The reaction mixture was left to stir at room temperature for 3 days, and then filtered. The residue was washed well with acetonitrile, and the filtrate evaporated. The crude product was then purified by RP-HPLC (System L) to afford Compound 15 (164 mg, 7%).

$\delta_H$ (CD$_3$OD, 300 MHz): 2.77 (2H, t, J 6Hz, C$\underline{H}_2$NH$_2$), 2.50–2.58 (10H, m, H$_2$NCH$_2$C$\underline{H}_2$N(C$\underline{H}_2$C$\underline{H}_2$NH)$_2$), 1.85 (6H, s, 2×C$\underline{H}_3$C=N), 1.23 (12H, s, 2×(C$\underline{H}_3$)$_2$CNH).

(b): Synthesis of Compound 16

To a solution of Compound 15 (201 mg, 0.583 mmol) in DMF (2 ml) were successively added Compound 1 (225 mg, 0.583 mmol). Py-BOP (258 mg, 0.583 mmol) and DIPEA (0.102 ml, 0.583 mmol) and the mixture was stirred for 2 hours at room temperature. The reaction mixture was diluted with ethyl acetate (50 ml), washed with saturated sodium bicarbonate, dried over sodium sulphate and concentrated in vacuo to leave a foamy residue. The above residue was dissolved in a mixture of TFA and water (95/5, v/v, 10 ml) and the solution stirred for 1 hour at room temperature. The title compound precipitated upon addition of diethyl ether (150 ml). It was collected and washed with diethyl ether, dried in vacuo and purified by RP-HPLC (System A).

Mass Spec. Analysis (ES+)

Theoretical molecular weight: 612.8

Experimental molecular weight [M+H]+612.4

Example 13

Synthesis of 3,311,11-tetramethyl-7-N-[4-N-(5-aminopentyl)amidosulphonyl)benzoyl) aminomethylcyclohexyl carbonyl]aminoethyl-4,7,10-triazatridecane-2,12-dione dioxime (Compound 17)

To a solution of Compound 7 (84 mg, $1.6 \times 10^{-4}$ mol), Compound 15 (65 mg, $1.89 \times 10^{-4}$ mol) and HBTU (61 mg, $1.6 \times 10^{-4}$ mol, 1 eq) in dry DMF (2 ml) under $N_2$, was added DIPEA (140 ml, $8.00 \times 10^{-4}$ mol, 5 eq). The reaction was stirred at room temperature for 3 hours and the crude mixture was purified by RP-HPLC (System L) to afford the desired product (56 mg, 41%). The title compound was obtained by TFA deprotection as described for Compound 3 and purified by RP-HPLC (System L) (19 mg, 39%).

Mass Spec. Analysis (ES+)

Theoretical molecular weight: 751.3

Experimental molecular weight [M/2+H ]+376.1

Example 14

Synthesis of 1-N- [4-(N-(5-aminopentyl)-amidosulphonyl)benzoyl-3,7-diazanonyl-1,9-diamine (Compound 18)

To a cold solution (−70° C.) of N,N'-bis(2-aminoethyl)-1,3-propanediamine (2 g, 12.48 mmol) in anhydrous dichloromethane (20 ml) was added dropwise, under $N_2$, a solution of di-tert-butyl dicarbonate in dichloromethane (4 ml). The reaction mixture was stirred at −70° C. for 0.5 hour and at room temperature for 18 hours. The solvent was removed in vacuo to give an oil which was chromatographed over silica gel (CH$_2$Cl$_2$/MeOH/NH$_3$, 80:20:2) yielding the mono-protected tetraamine (1.08 g, 33%).

A solution of Compound 1 (170 mg, 0.44 mmol) and N-hydroxysuccinimide (51 mg, 0.44 mmol) in anhydrous tetrahydrofuran (4 ml) was cooled to −10° C., under $N_2$. A 1M solution of DCC in dichloromethane (440 ml, 0.44 mmol) was added dropwise and the reaction mixture was stirred at room temperature for 1.5 h. The reaction mixture was then treated with a solution of the mono-protected tetraamine (95.6 mg, 0.37 mmol) in anhydrous THF (4 ml). After stirring at room temperature for 18 hours, the reaction mixture was reduced in vacuo. The white solid obtained was chromatographed over silica gel (CH$_2$Cl$_2$/MeOH/NH$_3$, 90:20:2) to give a colour less oil (120 mg, 52%). A solution of 35% HCl/MeOH 1:1 (2.3 ml) was added dropwise to a solution of the above oil (120 mg, 191 mmol) in methanol (0.7 ml) over 21 hours. The reaction mixture was stirred for a further 2 hours and the white solid formed was recovered by filtration, washed three times with methanol (1 ml) and dried in vacuo leading to a white powder of the hydrochloride salt of the title compound (94.7 mg, 86%).

Mass Spec. Analysis (ES+)

Theoretical molecular weight: 429.3

Experimental molecular weight [M/2+H]+215.3

Example 15

Synthesis of 1-N-[4-(N-(5-aminopentyl) amidosulphonyl]benzoyl-6-oxo-7,10,14-triazahexadecyl-1,16-diamine (Compound 19)

To a solution of the monoprotected tetraamine as described in Example 14 (161 mg, 0.62 mmol) and Z-aminocaproic acid (164 mg, 0.62 mmol) in DMF (3 ml)

was added HBTU (235 mg, 0.62 mmol) and DIPEA (539 ml, 3.1 mmol). The reaction mixture was stirred at room temperature, under $N_2$, for 23 hours then diluted with dichloromethane (10 ml), washed with $NaHCO_3$ (10 ml) and water (20 ml). The organic layer was reduced in vacuo and the residue was chromatographed over silica gel ($CH_2Cl_2$/ MeOH/$NH_3$, 70:30:2) to give a pale yellow oil (121.7 mg, 39%). To a solution of this oil (116 mg, 0.23 mmol) in anhydrous ethanol (3 ml) was added cyclohexene (232 ml, 2.3 mmol) and 10% palladium over charcoal (116 mg). The reaction mixture was heated at 60° C. for 2 hours, cooled to room temperature and then filtered. The residue was washed with methanol, the filtrates combined and reduced in vacuo to give a colourless oil (81.2 mg, 94.6%). To a solution of the oil (81.2 mg, 0.22 mmol) and Compound 1 (84.0 mg, 0.22 mmol) in DMF (3 ml) was added HBTU (82.6 mg, 0.22 mmol) and DIPEA (190 ml, 1.1 mmol). The reaction mixture was stirred at room temperature under $N_2$, for 5 hours then diluted with dichloromethane (15 ml), washed with $NaHCO_3$ (20 ml) and water (2×10 ml). The organic layer was reduced in vacuo and the residue was chromatographed over silica gel ($CH_2Cl_2$/MeOH/$NH_3$, 70:30:2) to give a white gum (73.5 mg, 45%). The title compound was obtained by acid deprotection as described for Compound 18, as a pale yellow solid (30.8 mg, 100%).

Mass Spec. Analysis (ES+)

Theoretical molecular weight: 542.3

Experimental molecular weight [M/2+H]+271.8

Example 16

Synthesis of 1-(4-(N-(5-aminopentyl)-amidosulphonyl)benzyl)-1,4,8,11-tetraazacyclotetradecane (Compound 20)

To a solution of mono-BOC-1,5-diaminopentane (0.5 ml, 2.40 mmol) in dichloromethane (5 ml) was added triethylamine (400 ml, 2.87 mmol, 1.2 eq). A solution of bromomethyl benzenesulphonyl chloride (0.648 g, 2.40 mmol, 1 eq) in dichloromethane (2 ml) was added dropwise with stirring for 3 hours. The reaction mixture was washed with water, and the organic phase was dried ($Na_2SO_4$), filtered and evaporated. The residue was purified by flash column chromatography (3:2 petrol:EtOAc) to afford the desired product as an oil (190 mg, 18%). To a solution of cyclam (170 mg, 8.49×10$^{-4}$ mmol, 7 eq) under $N_2$ in dry THF (5 ml) and dry ethanol (2 ml) was added sodium hydride (8 mg, 2×10$^{-4}$ mol, 2 eq). The reaction mixture was stirred for 30 mins, after which a solution of N-BOC-bromomethyl benzene-sulphonyl cadaverine (50 mg, 1.15×10$^{-4}$ mol) in THF (1 ml) was added. The reaction was monitored by TLC (70:30:1 $CH_2Cl_2$:MeOH:$NH_3$). When the reaction was judged to be complete, the solvent was removed in vacuo. The residue was taken up in dichloromethane, and washed twice with saturated sodium bicarbonate solution. The organic phase was dried ($Na_2SO_4$), filtered and evaporated. The crude residue was purified by RP-HPLC (System L) to afford the desired product (20 mg, 31%). The title compound was obtained by TFA deprotection as described for Compound 3 and purified by RP-HPLC (System L) (7 mg, 43%).

$\delta_H$ ($CDCl_3$, 300 MHz): 7.77 (2H, d, J 8.4 Hz, aromatic CH), 7.51 (2H, d, J 8.4 Hz, aromatic CH), 3.61 (2H, s, PhC$\underline{H}_2$), 2.55–2.96 (20H, m, $SO_2NHC\underline{H}_2$, $C\underline{H}_2NHBoc$, 8×cyclam $C\underline{H}_2N$), 1.33–1.54 (6H, m, —($C\underline{H}_2$)$_3$—).

Example 17

Synthesis of S-acetyl-mercaptoacetylglycylglycylglycine (Compound 21)

A solution of H-Gly-Gly-Gly-OH (1.28 g, 6.76 mmol), S-acetyl-thioglycolic acid pentafluorophenyl ester (Novabiochem, 2 g, 6.76 mmol) and DIPEA (1.14 ml, 6.76 mmol) in a mixture of DMF (25 ml) and water (12 ml), was stirred overnight at room temperature. The reaction mixture was filtered to remove some remaining H-Gly-Gly-Gly-OH, brought to pH2 with 1M aqueous HCl and evaporated to dryness. The residue was triturated with acetone to afford the title compound.

Mass Spec. Analysis (ES+)

Theoretical molecular weight: 305.3

Experimental molecular weight [M+H]+305.8

Example 18

Synthesis of N-[S-acetyl-mercaptoacatylglycylglycylalycylglycyl)-N'-(4-N-(5-aminopentyl)amidosulphonyl)benzoyl propane-1,3-diamine (Compound 23)

(a): Synthesis of N-4-(N-(5-N'-$^t$butoxycarbonyl aminopentyl)sulphonamido)benzoyl)-N'-fluorenylmethoxycarbonyl propane-1,3-diamine (Compound 22)

BOC-1,3-diaminopropane was reacted with Fmoc-OSu in dichloromethane in the presence of DIPEA, and the resulting product treated with 4M HCl in dioxane to afford Fmoc-1,3-diaminopropane hydrochloride in quantitative yield. To a solution of Fmoc-diaminopropane hydrochloride (1.1 g, 3.3 mmol), Compound 1 (1.27 g, 3.3 mmol) and Py-BOP (1.46 g, 3.3 mmol) in DMF (10 ml), was added DIPEA (1.15 ml, 6.6 mmol) and the mixture was stirred for 4 hours at room temperature. The reaction mixture was diluted with EtOAc (200 ml), washed with water, saturated aqueous sodium hydrogen carbonate, 1M aqueous potassium hydrogen sulphate, brine, and concentrated under reduced pressure to afford Compound 22 as a white solid that was triturated with hexane, collected by filtration and dried in vacuo.

(b): Synthesis of Compound 23

Compound 22 (1 g, 1.5 mmol) was treated with diethylamine (2 ml) in DMF for 1 hour at room temperature. The solution was concentrated to dryness and the resulting gum triturated in diethyl ether to afford a white solid. The solid was coupled to Compound 21 (370 mg) with Py-BOP as previously described for Compound 3 to afford a white solid after trituration in diethyl ether. The title compound was obtained by TFA deprotection and RP-HPLC as described for Compound 3.

Mass Spec. Analysis (ES+)

Theoretical molecular weight: 629.8

Experimental molecular weight [M+H]+629.3

Example 19

Synthesis of N-[6-hydrazinopyridine-3-carbonyl]-N'-(4-N-(5-aminopentyl)amidosulphonyl)benzoyl propane-1,3-diamine (Compound 24)

6-BOC-hydrazinopyridine-3-carboxylic acid N-hydroxysuccinimde ester was prepared according to Schwartz et al. (U.S. Pat. No. 5,206,370, 1993). It was then coupled to diaminopropane in DMF and purified by silica gel chromatography. The title compound was obtained by coupling the above with Compound 1, TFA deprotection and RP-HPLC purification as described for Compound 3.

Mass Spec. Analysis (ES+)

Theoretical molecular weight: 477.5

Experimental molecular weight [M+H]+477.3

Example 20

Synthesis of N,N'-bis-(2-hydroxybenzyl)-2-(4-N-(5-aminopentyl)amidosulphonyl)benzamidomethyl-2-methyl-propane-1,3-diamine (Compound 25)

To a solution of 2-[bis-(aminomethyl)]propylamine (0.5 g, 4.26 mmol) in dry dichloromethane (49 ml) under $N_2$ was added dry triethylamine (0.29 ml, 2.08 mmol). The resultant solution was cooled to −78° C., and a solution of BOC anhydride (0.465 g, 2.13 mmol, 0.5 eq) in dry dichloromethane (49 ml) was added dropwise over 1 hour. The mixture was allowed to warm to room temperature over several hours and then stirred overnight at room temperature, during which time a white cloudy suspension formed. 1M NaOH soln. (30 ml) was added, and the organic layer separated. The aqueous layer was then extracted with three portions of dichloromethane. The combined organic layers were dried ($MgSO_4$), filtered and evaporated to afford the desired product as a colourless oil (0.58 g, 63%). To a solution of mono-N-BOC-2-[bis-(aminomethyl)]propylamine (0.58 g, 2.67 mmol) in dry ethanol (27 ml) under argon was added salicylaldehyde (0.57 ml, 5.34 mmol, 2 eq). The mixture was heated at reflux temperature for 1 hour during which time a yellow solution formed. After cooling, the solvent was removed in vacuo to afford the desired product as a yellow oil (0.66 g, 58%).

To a solution of the above crude product (0.47 g, 1.11 mmol) in dry ethanol (15 ml) was added sodium borohydride (146 mg, 3.86 mml 3.5 eq). The mixture was stirred at room temperature for 2 hours, during which time the yellow colour disappeared to give a colourless solution. Water (3 ml) was added, and the ethanol/water was decanted off from the white oily solid which was formed. The ethanol was removed in vacuo, and the remaining aqueous phase was extracted with two portions of dichloromethane. The combined organic layers were dried ($MgSO_4$), filtered and evaporated to give a colourless oil. The crude oil was purified by flash column chromatography using a gradient of 70% EtOAc/petrol to 100% EtOAc, affording the desired product as a colourless oil (250 mg, 52%). The oil (105 mg, $2.45 \times 10^{-4}$ mol) was treated at room temperature for 1 hour with 9:1 $TFA:CH_2Cl_2$ (5 ml). The solvents were removed in vacuo to afford the desired product as an oil (109 mg, 100%).

To a solution of the above oil (109 mg, $2.45 \times 10^{-4}$ mol) and Compound 1 (95 mg, $2.45 \times 10^{-4}$ mol, 1 eq) in DMF (2 ml) under $N_2$ was added HBTU (93 mg, $2.45 \times 10^{-4}$ mol, 1 eq) and DIPEA (300 ml, 1.72 mmol, 7 eq). The reaction mixture was stirred for 24 hours and then diluted with dichloromethane before washing with three portions of 10% citric acid. The organic layer was then washed with two portions of saturated sodium bicarbonate solution and finally with one portion of brine. The organic layer was dried ($Na_2SO_4$), filtered and evaporated to afford a crude product. The crude reaction mixture was taken forward in to the next step without purification. The title compound was obtained by TFA deprotection as described for Compound 3 and purified by RP-HPLC (System L) (14 mg).

Example 21

Tc-99 mlabelling of Compounds 2–6, 8–11, 13, 14, 16–20, 25

A 0.1 ml aliquot of the compound dissolved in methanol or $H_2O$ (1 mg/ml; 7.5 mg/ml for Compound 14) was transferred to a nitrogen-filled 10 ml glass vial together with deoxygenated saline (0.9% w/v, 1 ml) and 0.035 ml aqueous NaOH (0.1M) (for Compound 20 1M NaOH was used). To this solution was added technetium generator eluate (1 ml, approx. 0.4 GBq) and then aqueous stannous chloride solution (0.1 ml, ca.10 μg). The labelling pH was 9.0–10.0 (pH11–12 for Compound 20). Vials were incubated at ambient laboratory temperature (15–25° C.) for 30 minutes to effect labelling. HPLC purification was performed (System C; System H for Compound 14; System N for Compounds 18, 19) to remove unlabelled starting material and radioactive impurities prior to testing. After purification the organic solvent was removed under vacuum and the sample was redissolved in about 5 ml 0.1M phosphate buffer pH7.4 to give a working concentration of 6–9 MBq/ml. Radiochemical purity was assessed before use by the thin layer chromatography (TLC) system described below:

i) ITLC SG 2 cm×20 cm eluted with 0.9% w/v saline ii) Whatman No. 12 cm×20 cm eluted with 50:50 v/v acetonitrile: $H_2O$ The labelled substrates remain at, or close to, the origin in TLC system (i) and move close to the solvent front in system (ii). When analysed by appropriate detection equipment the radiochemical purity is typically in excess of 85% labelled compound.

Example 22

Tc-99m labelling of Compound 23

A gluconate kit was reconstituted with technetium generator eluate (5 ml, 2 GBq) and allowed to incubate at room temperature for 15 minutes to effect labelling. An aliquot (0.1 ml) of the compound freshly dissolved in methanol (5 mg/ml) was transferred to a nitrogen-filled 10 ml glass vial together with 0.025 ml of aqueous NaOH (0.1M) and 2 ml of the $^{99m}$Tc-gluconate solution. The labelling pH was 9.0. Vials were incubated at room temperature for 30 minutes to effect labelling. Purification and assessment of radiochemical purity was carried out as for Example 21.

Example 23

Tc-99 mlabelling of Compound 24

A 0.1 ml aliquot of the compound dissolved in methanol (1 mg/ml) was transferred to nitrogen-filled 10 ml glass vial together with tricine dissolved in water (0.5 ml, 37.5 mg) and phosphinedynetris(benzene sulphonic acid)tris sodium salt dissolved in water (0.1 ml, 1 mg). To this solution was added technetium generator eluate (1 ml, approx 0.4 GBq) and then a solution of stannous chloride in 0.1M HCl (0.02 ml, ca 2 μg). The labelling pH was 4.5–5.5. Vials were incubated at 60° C. for 30 minutes to effect labelling. Purification and assessment of radiochemical purity was carried out as in Example 21.

Example 24

HPLC Systems

System A
  Column Waters C18 150×3.9 mm. Particle size 4 microns
  Gradient: Elution Profile 0–100%B in 22 min.
  Eluent A: 0.1% aqueous TFA
  Eluent B: acetonitrile
  Flow Rate: 1 ml/min
System B
  Column Waters C18 150×3.9 mm. Particle size 4 microns
  Gradient: Elution Profile 0–100%B in 22 min.
  Eluent A: 0.1% aqueous TFA
  Eluent B: acetonitrile
  Flow Rate: 3 ml/min
System C
  Column Waters C18 150×3.9 mm. Particle size 4 microns
  Gradient: Elution Profile 0–100%B in 22 min.
  Eluent A: 0.1% aqueous TFA
  Eluent B: 0.1% TFA in acetonitrile
  Flow Rate: 1 ml/min
System D
  Column Hamilton PRP-1
  Gradient: Elution Profile 0–100%B in 20 min.
  Eluent A: 0.1% aqueous TEA
  Eluent B: 0.1% TEA in acetonitrile
  Flow Rate: 1 ml/min
System E
  Column Hamilton PRP-1
  Gradient: Elution Profile 20–100%B in 15 min.
  Eluent A: 0.1% aqueous TEA
  Eluent B: 0.1% TEA in acetonitrile
  Flow Rate: 3 ml/min
System F
  Column Hamilton PRP-1
  Gradient: Elution Profile 0–100%B in 20 min.
  Eluent A: 0.1% aqueous TEA
  Eluent B: 0.1% TEA in acetonitrile
  Flow Rate: 3 ml/min
System G
  Column Hamilton PLRP-S
  Gradient: Elution Profile 0–100%B in 20 min.
  Eluent A: 2% aqueous $NH_3$
  Eluent B: acetonitrile
  Flow Rate: 6 ml/min
System H
  Column Hamilton PRP-1
  Gradient: Elution Profile 0–100%B in 20 min.
  Eluent A: 2% aqueous $NH_3$
  Eluent B: acetonitrile
  Flow Rate: 1 ml/min
System I
  Column Hamilton PRP-1
  Gradient: Elution Profile 0–65%B in 10 min.
  Eluent A: 5% aqueous $NH_3$
  Eluent B: acetonitrile
  Flow Rate: 2.5 ml/min
System J
  Column: Hamilton PRP-1
  Gradient: Elution Profile 0–65%B in 10 min.
  Eluent A: 5% aqueous $NH_3$
  Eluent B: acetonitrile
  Flow Rate: 2.5 ml/min
System K
  Column Hamilton PRP-1
  Gradient: Elution Profile 0–65%B in 10 min.
  Eluent A: 5% aqueous $NH_3$
  Eluent B: acetonitrile
  Flow Rate: 1 ml/min
System L
  Column Hamilton PRP-1
  Gradient: Elution Profile 0–100%B in 20 min.
  Eluent A: 2% aqueous $NH_3$
  Eluent B: acetonitrile
  Flow Rate: 3 ml/min
System M
  Column Hamilton PRP-1
  Gradient: Elution Profile 0–100%B in 22 min.
  Eluent A: 5% aqueous $NH_3$
  Eluent B: acetonitrile
  Flow Rate: 1 ml/min
System N
  Column Waters C18 150×3.9 mm. Particle size 4 microns
  Gradient: Elution Profile 0–100%B in 20 min.
  Eluent A: 0.1% aqueous TEA
  Eluent B: 0.1% TEA in acetonitrile
  Flow Rate: 1 ml/min Example 25

Incorporation into Human Plasma Clots

Incorporation of radiolabelled substrates into fibrin was investigated by induction of an in vitro human plasma clot in the following manner. To a siliconised 5 ml glass vial was added, (a) 800 μl of Tris(hydroxymethyl)aminomethane buffered saline pH 7.5 containing calcium chloride (50 mM Tris, 150 mM sodium chloride, 4 mM calcium chloride.), (b) 40 μl of physiological salt solution containing 100 units of thrombin per ml, (c) 400 μl of human plasma containing the radiolabelled substrate at a concentration of typically 10 kBq/ml. To aid induction of clot a roughened glass rod was added to the reaction vial. Control vials were prepared similarly but with the omission of thrombin and calcium chloride.

After incubation of the test solution at ambient laboratory temperature (ca. 20° C.) for 60 minutes the reaction was discontinued with the addition of about 400 μl of a cold solution of 33.5 mM ethylenediaminetetra-acetic acid disodium salt. Clots were separated from serum by vacuum filtration onto 0.45 μM nitrocellulose filters (pre-soaked in 1.5% BSA/tris(hydroxymethyl)aminoethane buffered saline pH 7.5 containing 0.1% Tween 20) and washed with about 2×10 ml of Tris(hydroxymethyl)aminomethane buffered saline pH 7.5 containing Tween 20 to a final concentration of 0.1%v/v. The proportion of total radioactivity was calculated by counting in suitable detection apparatus.

The fraction of radioactivity retained on the filter, after subtraction of the non-specific binding determined from the control, is a measure of incorporation into the filtered clots.

Example 26

Factor XIIIa Dependency of Incorporation

The radiolabelled substrates may be tested for Factor XIIIa mediated incorporation into fibrin and its analogues by a modification of the method of Dvilansky A. et al [Br. J. Haematol., 18 399–410(1970)]. The assay was changed by replacing the mercaptoethanol with aprotinin at a final concentration of 2 μg/ml, and dimethylcasein (DMC) was used instead of casein. Factor XIIIa specificity of the reaction is demonstrated by comparing human plasma with Factor XIII deficient plasma.

The modified assay was used to screen the test compounds (1 KBq/ml) and uptake after 60 minutes was determined. Compound activity was expressed as specific uptake by subtracting uptake in Factor XIII deficient plasma from normal plasma (see results table). The assay indicated that $^{99m}$Tc labelled compounds could be produced that had a range of levels of incorporation. These compounds were shown to be incorporated by a Factor XIII specific manner.

-continued

| compound | % retained in plasma clot assay (with thrombin) | % retained in plasma clot assay (no thrombin) | % specific uptake | % specific DMC casein uptake |
|---|---|---|---|---|
| Tc-Compound 24 | 14 | 0.2 | 13.8 | 22.5 |
| Tc-Compound 25 | 15 | 1.9 | 12.9 | 26 |

% retained in plasma clot assay (with thrombin) - % retained in plasma clot assay (no thrombin)

Example 27

Normal Rat Biodistribution

The resolution of a clot image is dependent on the combination of rate of incorporation of the radiopharmaceutical and its blood/tissues clearance rate. For this reason the biodistribution of several compounds has been determined in rats. Male Wistar (100–150 g) rats were injected i.v. with 0.1–0.2 ml of radiolabelled tracer solution (8 MBq/ml) and dissected at different times post-injection. The %ID in each of the selected tissues was measured. Some animals were kept in metabolism cages to be able to determine the %ID excreted in urine and faeces. The dissection times used for the majority of the agents was 2, 15, 30, 60, 240 min. Data are shown as %ID, Mean±SD, (n=3).

Results

Compound 3

|  | 2 min | 15 min | 30 min | 60 min | 240 min |
|---|---|---|---|---|---|
| Muscle | 23.6 + 0.9 | 4.87 + 0.6 | 1.53 + 0.71 | 1.14 + 0.48 | 0.8 + 0.17 |
| Blood | 19.29 + 1.7 | 1.45 + 0.38 | 0.59 + 0.07 | 0.31 + 0.02 | 0.11 + 0.07 |
| Kidney | 5.55 + 1 | 2.1 + 0.8 | 2.09 + 1.87 | 0.57 + 0.12 | 0.45 + 0.04 |
| Urine | 0.06 + 0.02 | 5.01 + 2.53 | 14.42 + 3.78 | 14.66 + 2.83 | 12.31 + 1.93 |
| Lung | 1.43 + 0.16 | 0.23 + 0.12 | 0.03 + 0.04 | 0.07 + 0.02 | 0.14 + 0.24 |
| Liver | 19.34 + 0.8 | 7.79 + 1.16 | 1.95 + 0.35 | 1.54 + 0.29 | 1.35 + 0.06 |
| GI Tract | 10.1 + 1.2 | 70 + 3.4 | 76.5 + 5.6 | 79.9 + 2.9 | 83.5 + 2.2 |
| Heart | 0.51 + 0.08 | n.d. | n.d. | n.d. | n.d. | n.d. not detectable.

Results

| compound | % retained in plasma clot assay (with thrombin) | % retained in plasma clot assay (no thrombin) | % specific uptake | % specific DMC casein uptake |
|---|---|---|---|---|
| Tc-Compound 2 | 2 | 0.3 | 1.7 | Not done |
| Tc-Compound 3 | 22 | 3.0 | 19 | 40 |
| Tc-Compound 4 | 3 | 0.4 | 2.6 | 2 |
| Tc-Compound 5 | 6 | 1.9 | 4.1 | 10 |
| Tc-Compound 6 | 2 | 0.5 | 1.5 | 13 |
| Tc-Compound 8 | 23 | 4.6 | 18.4 | 45 |
| Tc-Compound 9 | 20 | 4.5 | 15.5 | 29 |
| Tc-Compound 10 | 5 | 0.3 | 4.7 | 6 |
| Tc-Compound 11 | 16 | 3.2 | 12.8 | 24 |
| Tc-Compound 14 | 35 | 7.2 | 27.8 | N/A |
| Tc-Compound 16 | 2 | 0.8 | 1.2 | 1 |
| Tc-Compound 17 | 17 | 2.3 | 14.7 | 22.5 |
| Tc-Compound 20 | 4 | 0.6 | 3.4 | 8 |
| Tc-Compound 23 | 16 | 0.8 | 14.2 | 24.5 |

Compound 4

|  | 2 min | 30 min | 60 min | 240 min |
|---|---|---|---|---|
| Muscle | 22.6 + 0.8 | 5.27 + 0.4 | 2.26 + 0.05 | 1.94 + 0.35 |
| Blood | 10.33 + 1.2 | 0.98 + 0.18 | 0.43 + 0.07 | 0.21 + 0.08 |
| Kidney | 8.34 + 2.7 | 2.39 + 0.81 | 1.49 + 0.04 | 1.51 + 0.02 |
| Urine | 2.44 + 1.68 | 19.49 + 1.96 | 18.81 + 0.85 | 19.88 + 3.03 |
| Lung | 1.08 + 0.15 | 0.16 | 0.1 + 0.04 | 0.06 + 0.01 |
| Liver | 19.9 + 0.87 | 5.06 + 0.89 | 5.3 + 0.9 | 3.81 + 0.92 |
| GI Tract | 13.6 + 0.8 | 62.7 + 2.7 | 68.6 + 0.4 | 70.1 + 1.9 |
| Heart | 0.33 + 0.06 | 0.04 + 0.02 | 0.02 + 0.02 | 0.01 + 0.04 |

Compound 8

|        | 2 min       | 15 min      | 30 min      | 60 min      | 240 min     |
|--------|-------------|-------------|-------------|-------------|-------------|
| Muscle | 21.6 ± 2.08 | 3.97 ± 0.56 | 1.6 ± 0.82  | 1.22 ± 0.28 | 0.22 ± 0.31 |
| Blood  | 22.59 ± 1.44| 1.22 ± 0.06 | 0.55 ± 0.19 | 0.39 ± 0.05 | 0.1 ± 0.02  |
| Kidney | 4.56 ± 0.29 | 1.9 ± 0.95  | 1.8 ± 0.42  | 1.06 ± 0.22 | 0.85 ± 0.08 |
| Urine  | 0.13 ± 0.06 | 6.23 ± 1.23 | 7.18 ± 1.24 | 7.71 ± 0.49 | 8.55 ± 2.76 |
| Lung   | 1.61 ± 0.06 | 0.21 ± 0.03 | 0.1 ± 0.04  | 0.08 ± 0.01 | 0.05 ± 0.02 |
| Liver  | 19.6 ± 2.16 | 10.0 ± 0.86 | 4.53 ± 0.5  | 2.63 ± 0.38 | 1.39 ± 0.29 |
| GI Tract | 9.75 ± 1.2 | 70.9 ± 1.3  | 80.7 ± 2.4  | 85.4 ± 0.12 | 87.5 ± 2.8  |
| Heart  | 0.63 ± 0.17 | 0.06 ± 0.04 | n.d.        | 0.03 ± 0.01 | 0.01 ± 0.02 | n.d. not detectable.

Compound 16

|        | 2 min       | 30 min      | 60 min      | 240 min     |
|--------|-------------|-------------|-------------|-------------|
| Muscle | 32.9 + 0.97 | 4.63 + 0.25 | 1.51 + 0.53 | 0.55 + 0.08 |
| Blood  | 17.8 ± 1.78 | 2.20 ± 0.5  | 0.38 ± 0.14 | 0.04 ± 0.04 |
| Kidney | 10.55 ± 1.1 | 3.47 ± 0.71 | 1.80 ± 0.65 | 1.06 ± 0.06 |
| Urine  | 1.74 ± 1.05 | 48.0 ± 2.22 | 58.2 ± 8.87 | 58.9 ± 1.66 |

-continued

|          | 2 min       | 30 min      | 60 min      | 240 min     |
|----------|-------------|-------------|-------------|-------------|
| Lung     | 1.53 ± 0.12 | 0.31 ± 0.08 | 0.09 ± 0.03 | 0.04 ± 0.00 |
| Liver    | 5.61 ± 0.23 | 5.15 ± 0.75 | 3.07 ± 0.47 | 2.01 ± 0.11 |
| GI Tract | 6.61 ± 0.43 | 27.3 ± 3.45 | 31.6 ± 6.4  | 36.5 ± 1.5  |
| Heart    | 0.44 ± 0.09 | 0.06 ± 0.01 | 0.01 ± 0.01 | 0.00        |

Compound 17

|          | 2 min       | 15 min       | 30 min       | 60 min       | 240 min      |
|----------|-------------|--------------|--------------|--------------|--------------|
| Muscle   | 25.9 + 1.8  | 15.6 + 1.05  | 8.51 + 0.93  | 4.31 + 0.95  | 0.81 + 0.26  |
| Blood    | 18.5 + 1.06 | 9.46 + 0.24  | 5.7 + 0.42   | 2.23 + 0.15  | 0.09 + 0.02  |
| Kidney   | 12.3 + 0.53 | 7.32 + 0.76  | 7.1 + 1.89   | 3.77 + 0.73  | 5.1 + 0.99   |
| Urine    | 1.38 + 1.34 | 30.1 + 1.28  | 46.9 + 3.71  | 65.8 + 3.4   | 66.08 + 4.98 |
| Lung     | 1.69 + 0.1  | 0.9 + 0.16   | 0.54 + 0.07  | 0.28 + 0.02  | 0.1 + 0.01   |
| Liver    | 4.3 + 0.06  | 4.25 + 0.85  | 2.94 + 0.22  | 1.79 + 0.45  | 1 + 0.17     |
| Spleen   | 0.33 + 0.07 | 0.17 + 0.04  | 0.11 + 0.03  | 0.07 + 0.02  | 0.03 + 0.02  |
| GI Tract | 6.31 + 0.6  | 9.6 + 0.9    | 13.07 + 1.4  | 17.7 + 3.8   | 25.4 + 5.2   |
| Heart    | 0.34 + 0.17 | 0.27 + 0.06  | 0.17 + 0.04  | 0.07 + 0.02  | 0.01         |

Compound 24

|          | 2 min       | 15 min       | 30 min       | 60 min       | 240 min      |
|----------|-------------|--------------|--------------|--------------|--------------|
| Muscle   | 28.5 + 0.25 | 17.9 + 4.38  | 10.2 + 1.09  | 3.62 + 0.9   | 1.1 + 0.32   |
| Blood    | 18.2 + 1.39 | 7.11 + 1.29  | 3.86 + 0.62  | 1.6 + 0.57   | 0.29 + 0.06  |
| Kidney   | 10.2 + 3.07 | 4.11 + 1.31  | 2.52 + 1.1   | 1.4 + 0.38   | 0.92 + 0.37  |
| Urine    | 0.11 + 0.1  | 8.64 + 5.6   | 31.0 + 9.41  | 44.9 + 7.32  | 49.51 + 4.62 |
| Lung     | 1.99 + 0.12 | 0.78 + 0.16  | 0.39 + 0.06  | 0.18 + 0.06  | 0.05 + 0.02  |
| Liver    | 5.38 + 0.75 | 6.7 + 1.21   | 3.67 + 0.62  | 1.6 + 0.29   | 0.3 + 0.03   |
| GI Tract | 7.48 + 0.45 | 23.3 + 6.5   | 31.5 + 11.9  | 38.8 + 9.6   | 46.3 + 4.4   |
| Heart    | 0.73 + 0.1  | 0.3 + 0.08   | 0.13 + 0.03  | 0.06 + 0.03  | 0.02 + 0.01  |

Compound 25

|          | 2 min       | 15 min       | 30 min       | 60 min       | 240 min      |
|----------|-------------|--------------|--------------|--------------|--------------|
| Muscle   | 25.7 + 2.0  | 8.93 + 0.38  | 6.43 + 0.41  | 4.95 + 0.09  | 1.3 + 0.38   |
| Blood    | 23.0 + 2.9  | 3.9 + 0.17   | 2.12 + 0.34  | 1.84 + 0.19  | 0.62 + 0.16  |
| Kidney   | 5.37 + 1.3  | 7.13 + 0.4   | 5.6 + 0.1    | 4.24 + 0.4   | 3.19 + 0.1   |
| Urine    | 0.11 + 0.06 | 4.62 + 2.9   | 11.6 + 2.0   | 17.5 + 1.7   | 16.81 + 0.43 |
| Lung     | 3.42 + 0.39 | 1.37 + 0.03  | 1.17 + 0.01  | 0.96 + 0.11  | 0.21 + 0.05  |
| Liver    | 13.6 + 2.47 | 13.5 + 0.14  | 9.66 + 1.65  | 6.73 + 0.48  | 3.97 + 0.53  |
| GI Tract | 8.53 + 0.66 | 45.68 + 4.1  | 54.7 + 2.09  | 55.87 + 2.5  | 71.3 + 0.7   |
| Heart    | 0.74 + 0.1  | 0.16 + 0.01  | 0.1 + 0.03   | 0.08 + 0.03  | 0.02 + 0.01  |

Example 28

Incorporation into Clots Induced in a Rat Model
Rat Inferior Vena Cava Model (IVC)

The rats (Male Wistar, 250–350 g) were anaesthetised with 15% urethane. After laparotomy, the vena cava was isolated and freed of surrounding fat tissue. A platinum wire (1.5 cm×0.5 mm) was inserted into the inferior vena cava and 5 min post surgery 0.4 ml of ellagic acid ($1.2 \times 10^{-4}$ M) was injected intravenously through the femoral vein previously canulated, and the clot was allowed to form. The average weight of the clots formed in this model was around 27 mg, n=32, (5–50 mg range). The compounds were injected 5 min post-induction. After 60 min the animals were sacrificed and the clot removed, weighed and counted. Other tissues e.g. blood, lung, heart, were also dissected and counted. The uptake of tracer into the clot was determined as the relative concentration (cpm/g of clot by dose/g animal) and clot to background tissue.

Results

|  | Tc-Cpd3 | Tc-Cpd4 | Tc-Cpd8 | Tc-Cpd14 | Tc-Cpd16 | Tc-Cpd17 | Tc-Cpd24 | Tc-Cpd25 |
|---|---|---|---|---|---|---|---|---|
| % ID/g | 0.10 ± 0.02 | 0.18 ± 0.06 | 0.17 ± 0.09 | 0.18 ± 0.03 | 0.27 ± 0.06 | 0.32 ± 0.04 | 0.21 ± 0.02 | 0.29 ± 0.09 |
| Relative conc | 0.37 ± 0.1 | 0.52 ± 0.2 | 0.59 ± 0.31 | 0.54 ± 0.11 | 0.93 ± 0.16 | 1.1 ± 0.17 | 0.62 ± 0.1 | 0.8 ± 0.2 |
| Clot/Blood | 2 | 2.3 | 4.1 | 1.3 | 1.7 | 1.15 | 1.8 | 3.3 |
| Clot/Lung | 2.2 | 2.7 | 4.4 | 1.5 | 2.1 | 1.54 | 2.5 | 1.5 |
| Clot/Heart | 3.4 | 4.0 | 8.1 | 2.8 | 3.8 | 2.7 | 3.9 | 5 |
| Clot/Liver | 0.23 | 0.27 | 0.40 | 2.6 | 0.37 | 1.26 | 0.93 | 0.65 |

Abbreviations

BOC $^t$butoxycarbonyl
br.s broad singlet
d chemical shift in parts per million (ppm)
DCC dicyclohexylcarbodiimide
DIPEA diisopropylethylamine
DMAP dimethylaminopyridine
DMC dimethylcasein
DMF dimethylformamide
ES electrospray
EtOAc ethyl acetate
FAB fast atom bombardment
Fmoc fluorenylmethoxycarbonyl
HBTU O-benzotriazol-1-yl-N,N,N',N'-tetramethyluronium hexafluorophosphate
HPLC high performance liquid chromatography
hrs hours
Hz Hertz
J coupling constant
m multiplet
MALDI-tof matrix assisted laser desorption-ionised time of flight
meOH methanol
mins minutes
$^i$PrOH iso-propanol
Py-BOP benzotriazol-1-yloxytripyrrolidinophosphonium hexafluorophosphate
RCP radiochemical purity
RP-HPLC reverse phase high performance liquid chromatography
s singlet
t triplet
TEA triethylamine
TFA trifluoroacetic acid
THF tetrahydrofuran
TLC thin layer chromatography
Z benzyl carbamate

What is claimed is:

1. A composition comprising a conjugate of formula (metal complexing agent)—$((Y)_m$—A—$NHR)_k$, where:

k is a natural number;

Y is the same or different at different locations within the molecule and is independently chosen from: an A group, a $C_{4-8}$ cycloheteroalkylene group, a $C_{4-8}$ cycloalkylene group, a $C_{5-12}$ arylene group, a $C_{3-12}$ heteroarylene group, or a polyalkyleneglycol, polyactic acid or polyglycolic acid moiety, m is an integer of value 0–20, A is a 3–10 atom chain of units selected from —$CR_2$—, —CR═CR—, —C≡C—, —NRCO—, —CONR—, —$SO_2NR$—, —$NRSO_2$—, or —$CR_2ZCR_2$— where Z is —$CH_2$—, O, S, Se or —NR—, R is the same or different at different locations within the molecule and is independently chosen from H, $C_{1-4}$ alkyl, $C_{1-4}$ alkenyl, $C_{1-4}$ alkynyl, $C_{1-4}$ alkoxyalkyl or $C_{1-4}$ hydroxyalkyl, with the proviso that the complexing agent does not also have attached thereto a hypoxia localising moiety.

2. The composition of claim 1, wherein A is

—$NHCO(CH_2)_2Z(CH_2)_2$—, or

—$SO_2NH(CH_2)_2Z(CH_2)_2$—, or

—$(CH_2)_2Z(CH_2)_2$—.

3. The composition of claim 1, wherein Z is $CH_2$.

4. The composition of claim 1, wherein the at least one substituent has the formula —$(Y)_m$—A—$NH_2$.

5. The composition of claim 1, wherein the substituent has the formula

—$(Y)_b$—Ar—$SO_2NH(CH_2)_5NH_2$ where b is an integer of value 0 to 19 and Ar is an arylene or heteroarylene group.

6. The composition of claim 1, wherein the complexing agent is a metal chelating agent.

7. The composition of claim 6, wherein the metal chelating agent is a diaminedioxime.

8. A metal complex of one or more radiometal or paramagnetic metal ions with the composition of claim 1.

9. The metal complex of claim 8, wherein the radiometal is $^{99m}$Tc, $^{111}$In or $^{67}$Ga.

10. The metal complex of claim 8 for use in the diagnosis or therapy of thrombosis, embolism, atherosclerosis, inflammation or cancer.

11. A kit for the preparation of the metal complex of claim 8.

12. A vessel containing a unit dose for human administration of the metal complex of claim 8.

13. A method of preparing a composition for use in the diagnosis or therapy of thrombosis, atherosclerosis, inflammation or cancer, which method comprises bringing the metal complex of claim 8 into a form suitable for human administration.

* * * * *

UNITED STATES PATENT AND TRADEMARK OFFICE
CERTIFICATE OF CORRECTION

PATENT NO. : 6,653,299 B1
DATED : November 25, 2003
INVENTOR(S) : Forster et al.

It is certified that error appears in the above-identified patent and that said Letters Patent is hereby corrected as shown below:

Title page,
Item [73], Assignee, please delete "Nycomed Amersham PLC." and insert
-- Amersham PLC. -- in its place.

Column 30,
Line 8, after "1. A composition comprising a conjugate of formula
 (metal complexing Agent)—$((Y)_m$—A—NHR$)_k$,
where:" please insert the following paragraph:
-- the metal complexing agent is seleted from the group consisting of chelating agents selected from the group consisting of diaminedioximes, diaminedioxime amide donors, tetradentate ligands, $N_2S_2$ diaminedithiolos, $N_2S_2$ diamidedithiols, $N_2S_2$ amideaminedithiols, $N_3S$ thioltriamides, tetraamines, macrocyclic amine ligands, macrocyclic mide ligands, macrocyclic aminocarboxylate ligands, macrocyclic aminophosphonic acid ligands; and monodentate complexing agents that form stable complexes with the metal ion selected from the group consisting of hydrazines, phosphines, arsines and isonitriles; --.

Signed and Sealed this

Fifteenth Day of November, 2005

JON W. DUDAS
*Director of the United States Patent and Trademark Office*